(12) United States Patent
Saito et al.

(10) Patent No.: US 7,755,255 B2
(45) Date of Patent: Jul. 13, 2010

(54) ULTRASONIC PROBE

(75) Inventors: Koetsu Saito, Tokyo (JP); Junichi Takeda, Kanagawa (JP)

(73) Assignee: Panasonic Corporation, Osaka (JP)

(*) Notice: Subject to any disclaimer, the term of this patent is extended or adjusted under 35 U.S.C. 154(b) by 199 days.

(21) Appl. No.: 10/573,686

(22) PCT Filed: Sep. 30, 2004

(86) PCT No.: PCT/JP2004/014770
§ 371 (c)(1),
(2), (4) Date: Mar. 27, 2006

(87) PCT Pub. No.: WO2005/030055
PCT Pub. Date: Apr. 7, 2005

(65) Prior Publication Data
US 2007/0276248 A1    Nov. 29, 2007

(30) Foreign Application Priority Data
Sep. 30, 2003 (JP) .............................. 2003-342274

(51) Int. Cl.
*H04R 17/00* (2006.01)
(52) U.S. Cl. ............... 310/334; 600/459; 367/155; 367/157; 310/327; 310/346
(58) Field of Classification Search ............ 310/334, 310/346, 327
See application file for complete search history.

(56) References Cited
U.S. PATENT DOCUMENTS
5,295,487 A * 3/1994 Saitoh et al. ............ 600/459
(Continued)

FOREIGN PATENT DOCUMENTS
EP    0 637 470    2/1995
(Continued)

OTHER PUBLICATIONS
PCT International Search Report dated Nov. 22, 2004.
(Continued)

*Primary Examiner*—Walter Benson
*Assistant Examiner*—Bryan P Gordon
(74) *Attorney, Agent, or Firm*—Dickinson Wright PLLC (57) ABSTRACT

A technique that can make a heat radiation effect higher and makes even a transmission voltage of an ultrasonic diagnostic apparatus higher and then makes a diagnostic depth deeper is disclosed. According to this technique, an ultrasonic probe has: a plurality of piezoelectric elements 1 which are long in an X-direction, are arrayed in a y-direction and transmit and receive ultrasonic waves in a z-direction (diagnostic depth direction); a plurality of ground electrodes 2 and signal electrodes 3 which are placed on the front surfaces and the rear surfaces of the individual piezoelectric elements, respectively; a plurality of signal electrodes 4 for extracting respective signals from the individual signal electrodes; a backing load member 5 which has a function for mechanically holding the piezoelectric elements through the signal electrodes and attenuating the unnecessary ultrasonic signal as necessary; a plurality of sheet-shaped heat conduction members 6 which are embedded inside the backing load member and positively transmit the heat generated from the piezoelectric elements; and a heat radiating block 7 which is linked to the heat conduction members on the rear side of the backing load member and radiates the heat transmitted through the heat conduction members.

9 Claims, 4 Drawing Sheets

U.S. PATENT DOCUMENTS

| | | | |
|---|---|---|---|
| 5,545,942 A * | 8/1996 | Jaster et al. | 310/341 |
| 5,592,730 A * | 1/1997 | Greenstein et al. | 29/594 |
| 5,602,718 A | 2/1997 | Peszynski | |
| 5,622,175 A | 4/1997 | Sudol et al. | |
| 5,629,906 A | 5/1997 | Sudol et al. | |
| 6,822,374 B1 * | 11/2004 | Smith et al. | 310/334 |
| 2001/0021807 A1 * | 9/2001 | Saito et al. | 600/437 |
| 2006/0255686 A1 * | 11/2006 | Saito | 310/322 |

FOREIGN PATENT DOCUMENTS

| | | | |
|---|---|---|---|
| EP | 0637470 | | 2/1995 |
| JP | 5244690 | | 9/1993 |
| JP | 05244690 | * | 9/1993 |
| JP | 779498 | | 3/1995 |
| JP | 8251694 | | 9/1996 |
| JP | 9108220 | | 4/1997 |
| JP | 9108221 | | 4/1997 |
| JP | 10-126889 | | 5/1998 |
| JP | 10126889 | | 5/1998 |
| JP | 2000-165995 | | 6/2000 |
| JP | 2000165995 | | 6/2000 |

OTHER PUBLICATIONS

Microfilm of the specification and drawings annexed to the request of JP Utility Model Application No. 169394/1988(Laid-Open No. 91510/1990), Shimadzu Corp., p. 10, lines 6-13, Fig. 3, Jul. 20, 1990.

Microfilm of the specification and drawings annexed to the request of JP Utility Model Application No. 140880/1988(Laid-Open No. 61312/1990), Aloka Co., Ltd., p. 6, line 7 to p. 7, line 4, Fig. 1 May 8, 1990.

Chinese Office Action dated Feb. 15, 2008 with English translation.

* cited by examiner

ULTRASONIC PROBE

TECHNICAL FIELD

The present invention relates to an ultrasonic probe used in an ultrasonic diagnostic apparatus and the like.

BACKGROUND ART

Figure 8:
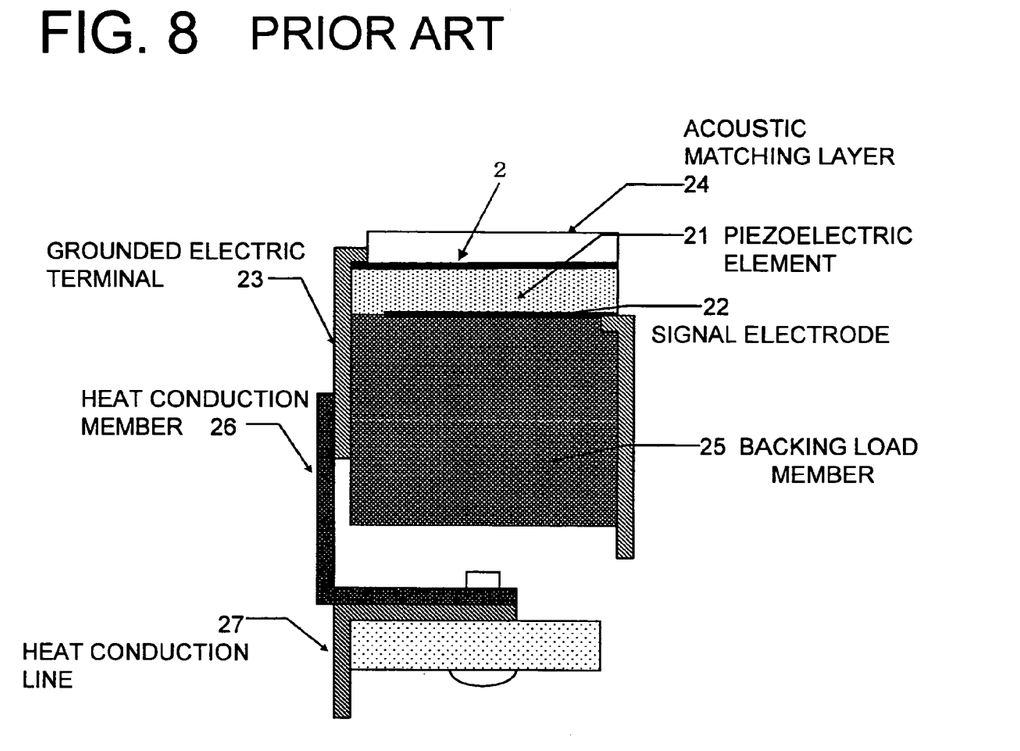
FIG. 8 is a schematic sectional view of a conventional ultrasonic probe.

As a conventional ultrasonic probe, as shown in FIG. 8, a plurality of piezoelectric elements 21 for transmitting and receiving ultrasonic waves are arrayed in a direction orthogonal to the drawing, and a ground electrode 2 and a signal electrode 22 are placed on the front surface and the rear surface of each of the piezoelectric elements 21, respectively (for example, refer to the following patent document 1). An acoustic matching layer 24 for efficiently transmitting and receiving the ultrasonic waves to and from a subject (living body) is formed on the front surface of the ground electrode 2. A backing load member 25, which has a function for attenuating the unnecessary ultrasonic waves transmitted from the piezoelectric element 21 and mechanically holding the piezoelectric element 21 through the signal electrode 22 is placed on the rear surface of the piezoelectric element 21 on the side opposite to the acoustic matching layer 24. The ground electrode 2 is linked to a grounded electric terminal 23, and the grounded electric terminal 23 is configured to be connected through a heat conduction member 26 to a heat conduction line 27.

In this ultrasonic probe, the main body of the ultrasonic diagnostic apparatus or the like applies an electric signal through a signal electrode (not shown) and the grounded electric terminal 23 to the respective signal electrodes 22 and ground electrodes 2. Consequently, the piezoelectric elements 21 are mechanically vibrated to transmit the ultrasonic waves, and the ultrasonic waves reflected from the subject such as the living body are received by the piezoelectric elements 21. The ultrasonic probe for the ultrasonic diagnostic apparatus that uses the living body as the subject is the sensor used for the diagnosis where it directly contacts with the inside of the living body and transmits the ultrasonic waves to the living body, and reflection waves reflected from the inside of the living body is again received by the ultrasonic probe, and its signal is processed by the main body, and a diagnostic image is displayed on a monitor.

In such a way that the ultrasonic probe for the ultrasonic diagnostic apparatus as mentioned above has no bad influence on the living body, the surface temperature of the ultrasonic probe in contact with the living body must be kept at the temperature which has no influence on the living body. As for the surface temperature of the ultrasonic probe, in situation that it does not contact with the living body, namely, in unused situation, and in situation that a transmission signal continues to be sent from the main body, heat is generated to raise the temperature. This main reason is assumed to result from the dielectric loss of the piezoelectric element 21 and the multiple reflection between the piezoelectric element 21, the acoustic matching layer 24 and an acoustic lens inside the probe. In this way, the surface temperature of the ultrasonic probe has the relation proportional to the transmission signal of the main body, and the limitation is actually executed such that the transmission signal is suppressed to the small value and adjusted so as not to raise the temperature. On the other hand, the transmission signal level and the depth at which the living body is diagnosed have the proportional relation. The suppression of the transmission signal to the small value results in the demerit that the diagnostic depth is also shallow. Thus, it is very important to make the transmission signal higher (make the diagnostic depth deeper) and also make the surface temperature of the ultrasonic probe lower.

In this way, the ultrasonic probe used in the ultrasonic diagnostic apparatus is in direct or indirect contact with the living body. Thus, in order to insure the safety, the surface temperature of the probe is regulated and must be managed. For this reason, by adjusting a voltage transmitted from the ultrasonic diagnostic apparatus body, it is set low and managed such that it is below the regulation temperature. On the other hand, there is the strong request for desiring to enlarge the diagnostic region of the ultrasonic diagnostic apparatus, especially, the depth direction. The foregoing transmission voltage and the enlargement of the depth direction have the proportional relation, which implies that as the transmission voltage is made higher, the diagnostic depth can be made deeper. Thus, it is desired to make the transmission voltage as high as possible. In view of those facts, the many trials of lowering the surface temperature of the ultrasonic probe have been tried in recent years. The structure shown in FIG. 8 is one of them and is configured to dissipate the heat from the grounded electric terminal 23 taken out from the ground electrode 2 of the piezoelectric element 21.

Patent Document 1: Japanese Patent Application publication (JP-A-Heisei, 5-244690) (FIG. 1)

However, the heat radiation in the configuration of the conventional ultrasonic probe is the heat radiation from a part of the grounded electric terminal 23 of the piezoelectric element 21, and there is a problem that it is not always sufficient.

DISCLOSURE OF THE INVENTION

In view of the problems in the conventional examples, the present invention has an object to provide an ultrasonic diagnostic apparatus that can make a heat radiation effect higher and make even a transmission voltage of an ultrasonic diagnostic apparatus higher and further make a diagnostic depth deeper.

In order to attain the above-mentioned object, the ultrasonic probe of the present invention is configured to have:

a piezoelectric element for transmitting and receiving ultrasonic waves;

a backing load member placed on a rear surface of the piezoelectric element; and a heat conduction material which is placed inside the backing load member or a part thereof and whose thermal conductivity is greater than a thermal conductivity of the backing load member.

With this configuration, the heat generated by the piezoelectric element can be absorbed and radiated by the material which is placed inside the backing load member or a part thereof and whose thermal conductivity is greater than the backing load member, and the temperature of an ultrasonic probe surface can be lowered. Thus, since even the transmission voltage of the ultrasonic diagnostic apparatus can be raised, the ultrasonic probe where a diagnostic depth can be made deeper can be obtained.

Also, the ultrasonic probe of the present invention is configured to have:

a plurality of piezoelectric elements, which are arrayed in one direction, for transmitting and receiving ultrasonic waves;

a backing load member placed on rear surfaces of the plurality of piezoelectric elements; and one or more sheet-shaped heat conduction materials which are placed in parallel along an array direction of the piezoelectric elements and a depth direction inside the backing load member and whose thermal conductivities are greater than a thermal conductivity of the backing load member.

With this configuration, the heat generated by the piezoelectric element can be absorbed and radiated by the material which is placed inside the backing load member and whose thermal conductivity is greater than the backing load member, and the temperature of the ultrasonic probe surface can be lowered. Thus, since even the transmission voltage of the ultrasonic diagnostic apparatus can be raised, the ultrasonic probe where the diagnostic depth can be made deeper can be obtained.

Moreover, the ultrasonic probe of the present invention is configured such that an end portion of the piezoelectric element side of the heat conduction material has the shape inclined to a surface of the backing load member side of the piezoelectric element.

With this configuration, the heat generated by the piezoelectric element can be absorbed and radiated by the material which is placed inside the backing load member and whose thermal conductivity is greater than the backing load member, and the temperature of the ultrasonic probe surface can be lowered. Thus, since even the transmission voltage of the ultrasonic diagnostic apparatus can be raised, the ultrasonic probe where the diagnostic depth can be made deeper can be obtained.

Moreover, the ultrasonic probe of the present invention is configured such that an angle between an inclination plane of the end portion on the piezoelectric element side of the heat conduction material and a direction vertical to the rear side of the piezoelectric element is 40 degrees or less or an angle where a critical angle of the ultrasonic waves is subtracted from 90 degrees.

With this configuration, the heat generated by the piezoelectric element can be absorbed and radiated by the material which is placed inside the backing load member and whose thermal conductivity is greater than the backing load member, and the temperature of the ultrasonic probe surface can be lowered. Thus, since even the transmission voltage of the ultrasonic diagnostic apparatus can be raised, the ultrasonic probe where the diagnostic depth can be made deeper can be obtained.

Moreover, the ultrasonic probe of the present invention is configured such that a heat radiating block which is connected to the heat conduction material and whose thermal conductivity is greater than the thermal conductivity of the backing load member.

With this configuration, the heat generated by the piezoelectric element can be absorbed by the material whose thermal conductivity is greater than the backing load member and can be radiated through the heat radiating block, and the temperature of the ultrasonic probe surface can be lowered. Thus, since even the transmission voltage of the ultrasonic diagnostic apparatus can be raised, the ultrasonic probe where the diagnostic depth can be made deeper can be obtained.

Moreover, the ultrasonic probe of the present invention is configured such that the heat radiating block is placed on the rear surface of the backing load member and wherein the heat conduction material is further placed between the heat radiating block and the backing load member.

With this configuration, the heat generated by the piezoelectric element can be absorbed by the material which is placed inside the backing load member or the part thereof and whose thermal conductivity is greater than the backing load member and can be radiated through the heat radiating block, and the temperature of the ultrasonic probe surface can be lowered. Thus, since even the transmission voltage of the ultrasonic diagnostic apparatus can be raised, the ultrasonic probe where the diagnostic depth can be made deeper can be obtained.

Moreover, the ultrasonic probe of the present invention is configured to include:

a plurality of piezoelectric elements which are divided by division grooves in one direction and transmit and receive ultrasonic waves;

a backing load member placed on rear surfaces of the plurality of piezoelectric elements; and block-shaped heat conduction materials which are placed on a rear surface of the backing load member and are greater than a thermal conductivity of the backing load member, wherein the division grooves are formed on the backing load member at depths where they do not reach the heat conduction materials.

With this configuration, the heat generated by the piezoelectric element can be absorbed and radiated by the material which is placed on the rear surface of the backing load member and whose thermal conductivity is greater than the backing load member, and the temperature of the ultrasonic probe surface can be lowered. Thus, since even the transmission voltage of the ultrasonic diagnostic apparatus can be raised, the ultrasonic probe where the diagnostic depth can be made deeper can be obtained.

Moreover, the ultrasonic probe of the present invention is configured to include:

a plurality of piezoelectric elements which are divided by division grooves in one direction and transmit and receive ultrasonic waves;

a backing load member placed on rear surfaces of the plurality of piezoelectric elements; and block-shaped heat conduction materials which are placed on a rear surface of the backing load member and are greater than a thermal conductivity of the backing load member, wherein the division grooves are formed at depths where they reach the heat conduction materials and wherein the backing load member is formed on a concave and convex surface formed on surfaces of the heat conduction materials through the division grooves.

With this configuration, the heat generated by the piezoelectric element can be absorbed and radiated by the material which is placed on the rear surface of the backing load member and whose thermal conductivity is greater than the backing load member, and the temperature of the ultrasonic probe surface can be lowered. Thus, since even the transmission voltage of the ultrasonic diagnostic apparatus can be raised, the ultrasonic probe where the diagnostic depth can be made deeper can be obtained.

Moreover, the ultrasonic probe of the present invention is configured such that as the heat conduction material, any material of PGS graphite sheet with high degree of orientation where polymeric film is graphitized, graphite, carbon nanotube, aluminum nitride, boron nitride, silicon carbide, beryllium oxide, copper and aluminum is used.

With this configuration, the heat generated by the piezoelectric element can be absorbed and radiated by the material whose thermal conductivity is greater than the backing load member, and the temperature of the ultrasonic probe surface can be lowered. Thus, since even the transmission voltage of the ultrasonic diagnostic apparatus can be raised, the ultrasonic probe where the diagnostic depth can be made deeper can be obtained.

According to the present invention, the heat generated by the piezoelectric element can be absorbed and radiated by the material whose thermal conductivity is greater than the backing load member, and the temperature of the ultrasonic probe surface can be lowered. Thus, since even the transmission voltage of the ultrasonic diagnostic apparatus can be raised, the diagnostic depth can be made deeper.

BEST MODE FOR CARRYING OUT THE INVENTION

First Embodiment

Figure 1:
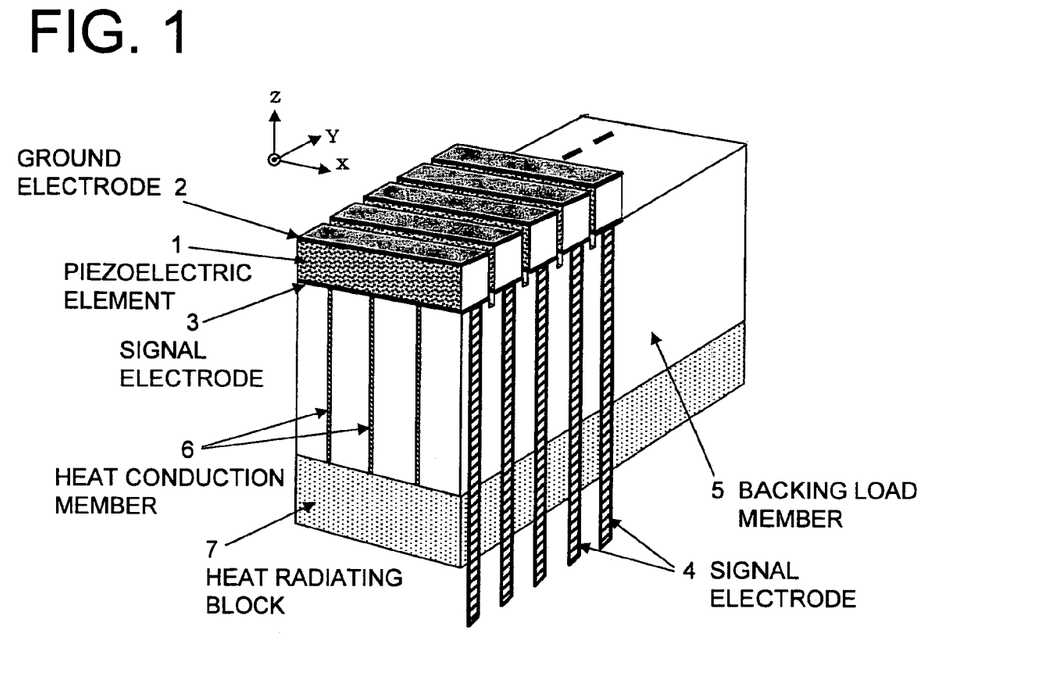
FIG. 1 is a schematic perspective view of an ultrasonic probe in a first embodiment of the present invention.
Figure 2:
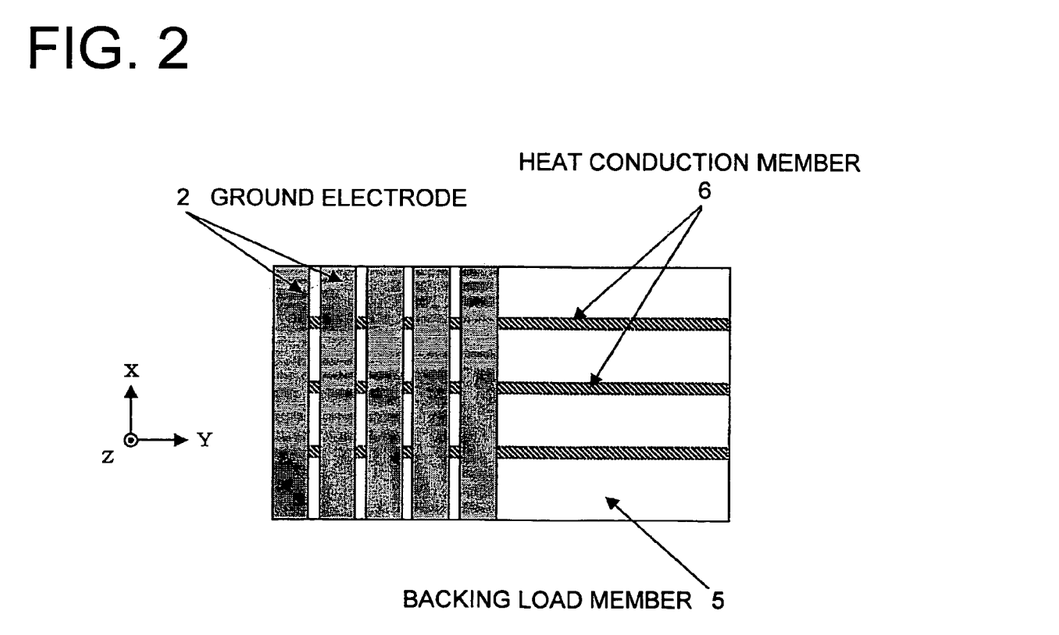
FIG. 2 is a schematic plan view of the ultrasonic probe in the first embodiment of the present invention.

An ultrasonic probe of an embodiment of the present invention will be described below with reference to the drawings. The ultrasonic probe in the first embodiment of the present invention is shown in FIG. 1 and FIG. 2. FIG. 1 shows the perspective view, and FIG. 2 shows the plan view when FIG. 1 is viewed from above.

In FIG. 1 and FIG. 2, the ultrasonic probe in the first embodiment is provided with: a plurality of piezoelectric elements 1 which are long in an X-direction, and arrayed in a y-direction and transmit and receive ultrasonic waves in a z-direction (diagnostic depth direction); a plurality of ground electrodes 2 and signal electrodes 3 which are placed on the front surfaces and the rear surfaces of the individual piezoelectric elements 1, respectively; a plurality of signal electrodes 4 for extracting respective signals of the individual signal electrodes 3; a backing load member 5 which has a function for mechanically holding the piezoelectric elements 1 through the signal electrodes 3 and attenuating the unnecessary ultrasonic signal as necessary; a plurality of (3 sheets in FIG. 1 and FIG. 2) of sheet-shaped heat conduction members 6 which are embedded inside the backing load member 5 and positively transmit the heat generated from the piezoelectric elements 1; and a heat radiating block 7 which is linked to the heat conduction members 6 on the rear side of the backing load member 5 and radiates the heat transmitted through the heat conduction members 6. The heat radiating block 7 is in contact with or adhered to the heat conduction members 6 so as to be able to attain the thermal conduction. A PZT-based piezoelectric ceramic or single crystal and the like are used for the piezoelectric element 1. The ground electrode 2 and the signal electrode 3 are formed on the front surface and the rear surface of the piezoelectric element 1, respectively, by evaporating or sputtering gold and silver or baking silver.

Also, although not shown, it may be configured to form one or more acoustic matching layers for efficiently transmitting and receiving the ultrasonic waves through the ground electrodes 2 on the front surface side of the piezoelectric elements 1, as necessary, and further place an acoustic lens for converging ultrasonic beams on the front surface of this acoustic matching layer.

Also, the ultrasonic waves transmitted from the piezoelectric element 1 are transmitted to the backing load member 5 and the heat conduction member 6. However, the ultrasonic waves transmitted to the backing load member 5 and the heat conduction member 6 is unnecessary. Thus, the present invention is designed such that it is attenuated by the absorption or dispersion inside the backing load member 5 and it is not again returned to the piezoelectric element 1. Also, so as to be extended in the depth direction inside the backing load member 5, and with the plurality of sheet-shaped heat conduction members 6 placed in parallel along the array direction of the piezoelectric elements 1, it is structured such that the ultrasonic waves are dispersed in the backing load member 5 so as not to be returned to the piezoelectric elements 1.

FIG. 1 and FIG. 2 are designed such that the 3 heat conduction members 6 are placed inside the backing load member 5. The number of the heat conduction members 6 placed inside the backing load member 5 or a part thereof may be one or more. However, when the ultrasonic waves from the piezoelectric element 1 are reflected by the heat conduction member 6, the number which has no bad influence is required.

Also, in FIG. 1 and FIG. 2, the heat conduction members 6 are configured to be continuously linked in the same direction as the array direction Y of the piezoelectric elements 1 and separated in a direction X orthogonal thereto. This is intended to attain the structure where the heats generated from the individual piezoelectric elements 1 are easily uniformly absorbed. In addition, the heat conduction members 6 may be placed even in the direction X orthogonal to the array direction Y of the piezoelectric elements 1. However, in that case, the heat conduction members 6 are required to be placed such that their number is equal to the array number of the piezoelectric elements 1, or placed at the intervals of one or several piezoelectric elements 1. Moreover, as another method, a large number of needle heat conduction members 6 may be two-dimensionally arrayed inside the backing load member 5.

The heat conduction member 6 is desired to have the thermal conductivity that is at least greater than the value of the backing load member 5. Usually, as the backing load member 5, the element where tungsten, alumina or glass or polymer hollow body to increase attenuation is filled in the polymeric material such as synthetic rubber in which ferrite powder is filled, or epoxy resin or urethane rubber is used. They are produced for the sake of obtaining the material having the large attenuation, and the thermal conductivity is not considered at all. Thus, the thermal conductivity is the very small value of about 1 W/mK. Because of the material unsuitable for the conduction of the heat, the effect of the heat radiation is small. The heat conduction member 6, if using the material having the thermal conductivity that is at least greater than the backing load member 5, has the effect. Moreover, in order to further improve the effect of the heat radiation, the material whose thermal conductivity is more than 10 times that of the backing load member 5 may be used. As the material of the heat conduction member 6, the material whose thermal conductivity is high (60 to 600 W/mK), such as PGS graphite sheet with high degree of orientation where polymeric film is graphitized, graphite, carbon nano-tube, aluminum nitride, boron nitride, silicon carbide, beryllium oxide, copper, aluminum and the like, is desired to be used.

Moreover, for the heat conduction member 6, in the case of the configuration in direct contact with the signal electrode 3 of the piezoelectric element 1, the material that can be electrically insulated is used. However, the heat conduction member 6 can be attained by using the electrically conductive or insulating material by installing the configuration that can electrically insulate the signal electrode 3 and the heat conduction member 6, for example, the configuration where the insulating adhesive such as epoxy resin is thinly coated between the signal electrode 3 and the heat conduction member 6, or the insulating layer such as polyimide film.

Also, the heat absorbed by the heat conduction member 6 is transmitted to the heat radiating block 7 and radiated. However, as this heat radiating block 7, the same material as the heat conduction member 6 may be used. Also, the heat conduction member 6 and the heat radiating block 7 may be integrally configured, and may be adhesively configured.

Also, the heat conduction member 6 is configured such that the heat can be transmitted from the rear surface of the backing load member 5 to the heat radiating block 7. However, the heat conduction member 6 may be extended to the side of the backing load member 5 so that this extended heat conduction member 6 is connected to the heat radiating block 7. The heat radiating block 7 in this case is not required to be located on the rear surface of the backing load member 5. Even the configuration where it is placed on the side of the backing load member 5 or on the separated position can obtain the similar effect.

With the above-mentioned configuration, the heat generated in the piezoelectric element 1 and the heat generated by the multiple reflection of the ultrasonic waves can be absorbed and radiated by the heat radiating block 7 that is connected so as to enable the heat to be transmitted through the heat conduction member 6 placed inside the backing load member 5 or the part thereof. Thus, this has the effect that the surface temperature of the ultrasonic probe can be decreased. Hence, the transmission voltage of the ultrasonic diagnostic apparatus can be made higher, thereby making the diagnostic depth deeper.

By the way, in the first embodiment, the case of the configuration where the 3 heat conduction members 6 are placed inside the backing load member 5 in the same direction as the array direction Y of the piezoelectric elements 1. However, in addition, even in the configuration where the heat conduction members 6 are placed in the direction X orthogonal to the array direction Y of the piezoelectric elements 1, or in the configuration where one or more needle heat conduction members 6 are placed, the similar effect is obtained. Also, in the first embodiment, the case of the so-called array type where the plurality of piezoelectric elements 1 are arrayed is explained. However, in addition, even in the case of the array type where the piezoelectric element 1 is arrayed singly or two-dimensionally, the similar effect is obtained.

Second Embodiment

Figure 3:
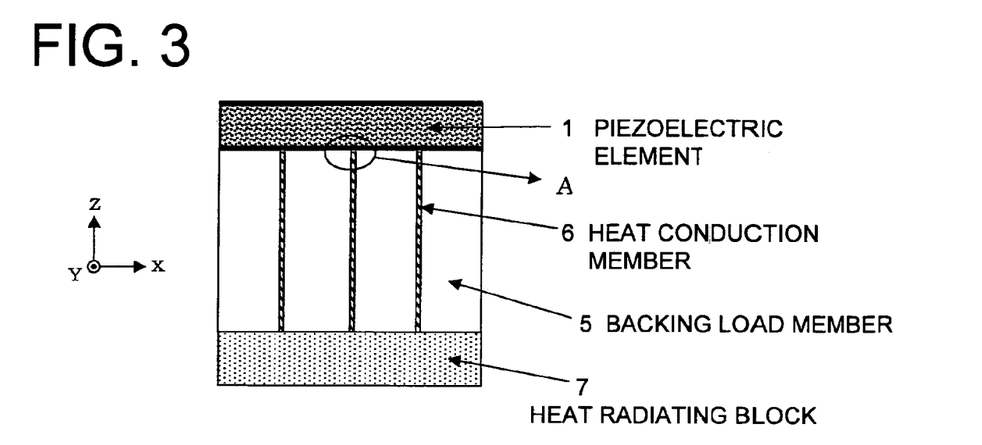
FIG. 3 is a schematic sectional view of an ultrasonic probe in a second embodiment of the present invention.
Figure 4:
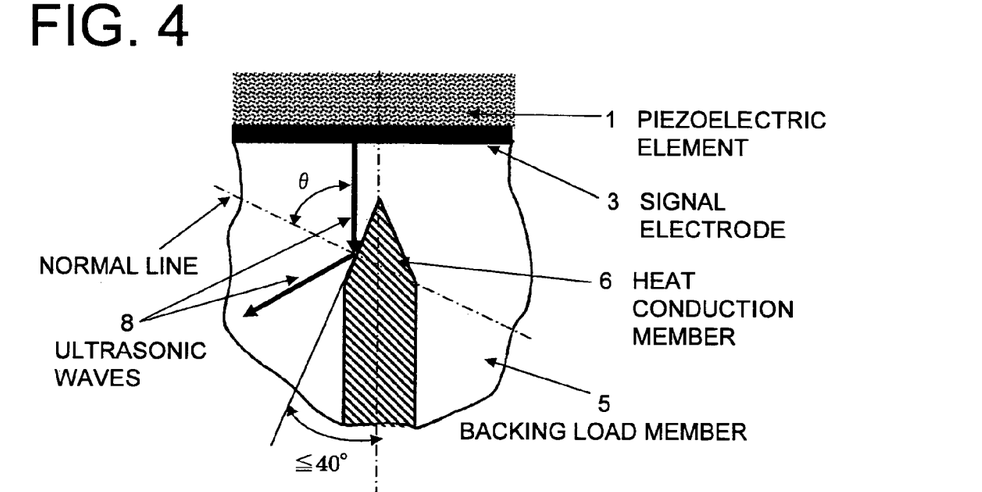
FIG. 4 is an enlarged view of an A-portion in FIG. 3.

Next, an ultrasonic probe in the second embodiment of the present invention is shown in FIG. 3 and FIG. 4. By the way, FIG. 4 shows the view where the A-portion of FIG. 3 is enlarged. The configurations of FIG. 3 and FIG. 4 are omitted here because they are equal to the configuration and operation explained in the first embodiment, and the feature of the second embodiment is explained. The second embodiment is characterized in that the end portion (tip portion) on the piezoelectric element 1 side of the heat conduction member 6 has the shape inclined to the surface of a backing load member 5 side of the piezoelectric element 1.

In such configuration, the piezoelectric element 1 is mechanically vibrated by the voltage applied to the signal electrode 3 and the ground electrode 2 (refer to FIG. 1) which are placed on the front surface and the rear surface of the piezoelectric element 1, respectively, and the ultrasonic waves is generated on both sides of the ground electrode 2 side and the signal electrode 3 side. Thus, the generated ultrasonic waves is also transmitted to the backing load member 5 and further transmitted to the portion of the heat conduction member 6 and reflected from the inclination plane of the tip of the heat conduction member 6 such as ultrasonic waves 8 shown in FIG. 4. Moreover, the ultrasonic waves 8 reflected from the inclination plane of the tip of the heat conduction member 6 are again transmitted inside the backing load member 5.

For this reason, if the angle of the inclination plane of the tip of the heat conduction member 6 (the angle to the direction where the ultrasonic waves 8 emitted from the piezoelectric elements 1 are transmitted in the depth direction of the backing load member 5 (the direction vertical to the rear surfaces of the piezoelectric elements 1) is set to be equal to or higher than the angle close to 45 degrees, the ultrasonic waves 8 are transmitted in the direction of the adjacent heat conduction member 6 at the angle close to 45 degrees and again reflected, and the ultrasonic waves 8 have the possibilities of the returns to the piezoelectric elements 1, which leads to the reduction in the resolution of an ultrasonic image. Also, if it is set at the angle of 45 degrees or more, this similarly leads to the route where the ultrasonic waves 8 are returned to the piezoelectric elements 1. The ultrasonic waves 8 that are again returned to those piezoelectric elements 1 are the unnecessary ultrasonic waves, which consequently act as noise for the ultrasonic image and reduce the resolution. Depending on the case, there is the possibility of an erroneous diagnosis on diagnosis. Thus, such necessary ultrasonic waves must be designed so as not to be returned to the piezoelectric elements 1.

So, if the angle of the inclination plane of the tip of the heat conduction member 6 is below 45 degrees, in principle, the reflected ultrasonic waves 8 is not returned to the piezoelectric element 1. However, the ultrasonic waves 8 have the property of diffusion. Thus, in this diffusion case, even in the case below 45 degrees, there is the case where the ultrasonic waves 8 are returned to the piezoelectric element 1. So, the angle of the inclination plane of the tip of the heat conduction member 6 is set below 40 degrees by considering the diffusion of the ultrasonic waves 8. Setting this angle attains the configuration where the ultrasonic waves 8 are not returned to the piezoelectric element 1. FIG. 3 and FIG. 4 show the heat conduction member 6 under the configuration where the inclination is formed on both sides (±X direction).

On the other hand, when the ultrasonic waves 8 are transmitted to the backing load member 5 and inputted to the inclination plane of the tip of the heat conduction member 6, a part of the ultrasonic waves is transmitted through the heat conduction member 6, and the other ultrasonic waves is reflected and transmitted to the backing load member 5. However, although this is already known, when the angle of the inclination plane of the tip of the heat conduction member 6 becomes a certain angle or more, the ultrasonic waves 8 transmitted through the backing load member 5 are not inputted to the inside of the heat conduction member 6. In short, the so-called critical angle where all of them are reflected from the inclination plane of the heat conduction member 6 is established. In the heat conduction member 6, the attenuation coefficient of the ultrasonic waves is not so much large, differently from the backing load member 5. Thus, there remains the possibility that the ultrasonic waves transmitted through the heat conduction member 6 are again returned to the piezoelectric elements 1. Hence, if possible, the configuration where the ultrasonic waves are not transmitted through the heat conduction member 6 is desired.

For example, the case where the so-called ferrite rubber of the rubber material in which the typically known ferrite powder is filled is used as the backing load member 5, and the typical graphite is used as the heat conduction member 6 is explained. In FIG. 4, when the angle to the normal line of the inclination plane when the ultrasonic waves 8 are emitted from the piezoelectric elements 1, transmitted through the backing load member 5 and inputted to the inclination plane of the tip of the heat conduction member 6 is assumed to be θ0, the angle θ0 when all of the ultrasonic waves are reflected on the inclination plane is referred to as a critical angle θ, and the critical angle θ is calculated by the following equation (1).

$$\text{Critical Angle } \theta = \sin^{-1}(C1/C2) \quad (1)$$

C1: Sound Speed of Backing Load Member 5 (Ferrite Rubber)

C2: Sound Speed of Heat Conduction Member 6 (Graphite)

C1<C2 (Case of Heat Conduction Member 6 from Backing Load Member 5)

Here, the sound speed C1 of the backing load member 5 (ferrite rubber) is about 1900 m/s, and the sound speed C2 of the heat conduction member 6 (graphite) is about 3200 m/s. When the critical angle θ is calculated from those sound speeds C1, C2, it is 36.4 degrees. When it becomes this angle or more, all of the ultrasonic waves 8 are perfectly reflected from the inclination plane of the heat conduction member 6, and they are not inputted to the inside of the heat conduction member 6. Here, as is known from FIG. 4, the angle between the ultrasonic waves 8 transmitted substantially vertical to the backing load member 5 from the piezoelectric elements 1 and the inclination plane of the heat conduction member 6 is 90 degrees—the critical angle θ. Thus, the angle of the inclination plane of the tip of the heat conduction member 6 may be configured to be equal to or less than (90 degrees—the critical angle θ). Even in the combination except the materials of the backing load member 5 and the heat conduction member 6 which are used as the example, if the materials explained in the first embodiment are used, the sound speed of the heat conduction member 6 is faster than the sound speed of the backing load member 5. Thus, the equation (1) is set.

With the above-mentioned configuration, the heat generated in the piezoelectric element 1 and the heat generated by the multiple reflection can be transmitted through the heat conduction member 6 placed inside the backing load member 5 or the part thereof. Moreover, even if the ultrasonic waves 8 inside the backing load member 5 are reflected from the heat conduction member 6, they are designed so as not to be again returned to the piezoelectric elements 1. Thus, this has the effect that the deterioration in the resolution can be protected and the surface temperature of the ultrasonic probe can be lowered. Hence, since the transmission voltage of the ultrasonic diagnostic apparatus can be made higher, the diagnostic depth can be made deeper.

By the way, in the second embodiment, the configuration where the inclination plane of the tip of the heat conduction member 6 is formed on both sides (±X direction) is explained. However, in addition to this, even if the inclination of the heat conduction member 6 is formed only on one side or even if the configuration of a conic shape is used, the similar effect is obtained.

Third Embodiment

Figure 5:
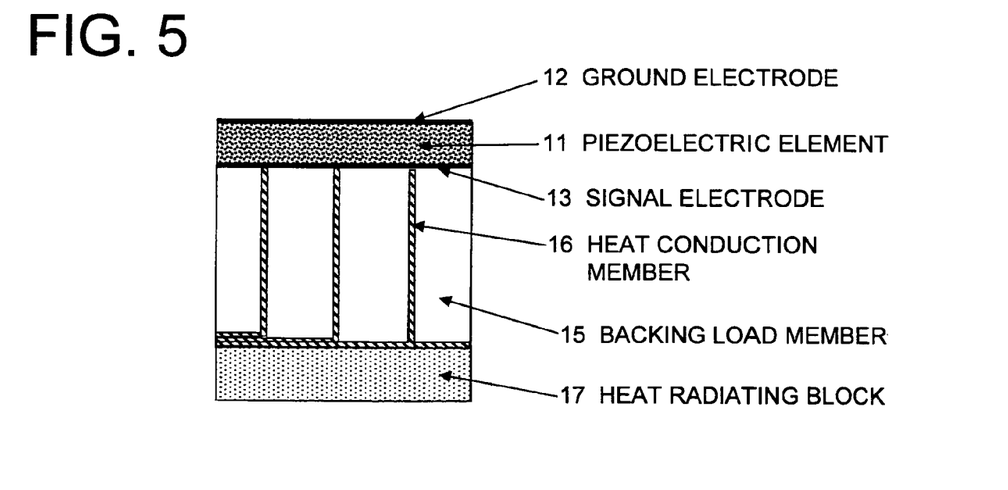
FIG. 5 is a schematic sectional view of an ultrasonic probe in a third embodiment of the present invention.

Next, the ultrasonic probe in the third embodiment of the present invention is shown in FIG. 5. The configuration of FIG. 5 is equal to the configuration and operation explained in the first embodiment. Thus, it is omitted here, and the feature of the third embodiment is explained. In the third embodiment, a heat conduction member 16 is further placed between a heat radiating block 17 and a backing load member 15.

As the heat conduction member 16, a material having thermal conductivity greater than that of the backing load member 15 is used, and the heat absorbed in the heat conduction member 16 is radiated in the heat radiating block 17. However, in the case where the heat conduction member 6 and the heat radiating block 17 can be integrally configured, there is no problem. However, depending on the case, there is the case where they cannot be always integrated. For example, in the case of using the PGS graphite sheet with the high degree of orientation where the polymeric film whose thermal conductivity is very high (600 to 800 W/mk) is graphitized as the heat conduction member 16, the same material cannot be used to configure the heat radiating block 17. In the heat conduction member 16, the contact area with the heat radiating block 17 is small. Thus, in order to make the heat radiation effect higher by further increasing the efficiency when the heat is transmitted from the heat conduction member 16 to the heat radiating block 17, the heat conduction member 16 is configured to be placed even on the rear surface of the backing load member 15.

Such configuration can be easily configured by using a sheet-shaped component of PGS graphite with high degree of orientation where the polymeric film is graphitized as the material of the heat conduction member 16. Moreover, the material different from the heat conduction member 16 is used to place the heat radiating block 17. With such configuration, the contact area between the heat conduction member 16 and the heat radiating block 17 can be made larger, thereby carrying out the effective heat radiation.

Also, a piezoelectric element 11 is mechanically vibrated by the voltage applied to a signal electrode 13 and a ground electrode 12 that are placed on both surfaces of the piezoelectric element 11, and the ultrasonic waves are generated on both of the sides (the ground electrode 12 side and the signal electrode 13 side). However, the generated ultrasonic waves 8 are configured such that they are attenuated inside the backing load member 15 and it is not returned to the piezoelectric element 11. Also, the heat conduction member 16 is placed inside the backing load member 15 or a part thereof, and the heated generated from the piezoelectric element 11 is absorbed and radiated.

By the way, in the third embodiment, the configuration where the sheet-shaped element is placed as the heat conduction member 16 is explained. However, in addition to this, when the heat conduction member 16 is processed from a block and placed in the shape of the heat conduction member 16 as shown in FIG. 5, the similar effect is obtained.

Fourth Embodiment

Figure 6:
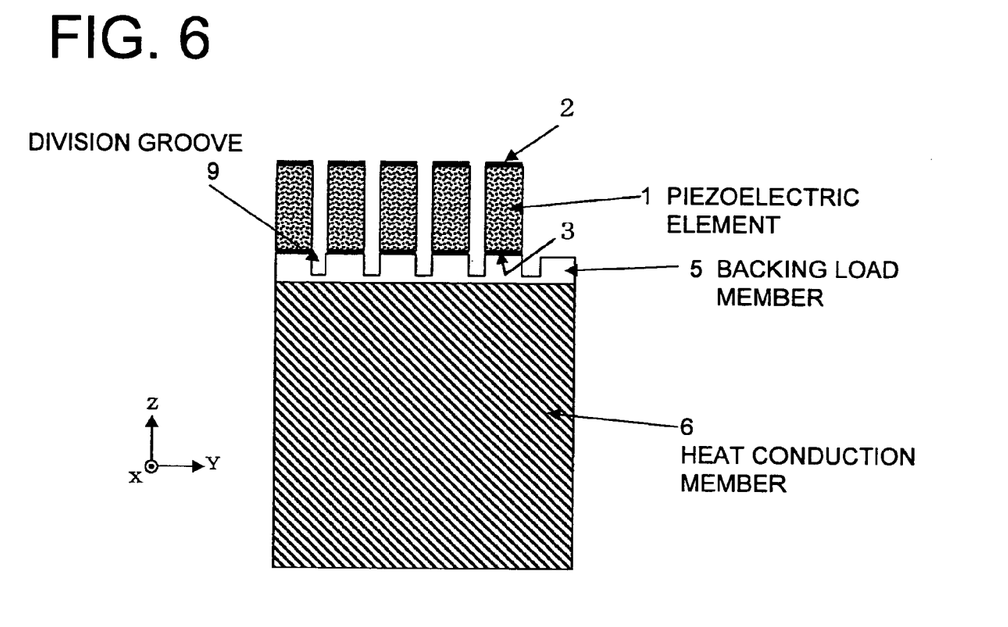
FIG. 6 is a schematic sectional view of an ultrasonic probe in a fourth embodiment of the present invention.

Next, an ultrasonic probe in the fourth embodiment of the present invention is shown in FIG. 6. The configuration of FIG. 6 is similar to that shown in the sectional view when the piezoelectric element 1 shown in FIG. 1 is viewed from the X-direction. Since it is equal to the configuration and operation explained in the first embodiment, it is omitted here, and the feature of the fourth embodiment is explained.

In FIG. 6, for the piezoelectric element 1 where the signal electrode 3 and the ground electrode 2 are placed on both of the surfaces thereof, a backing load member 5 is placed on the signal electrode 3 side, and the block-shaped heat conduction member 6 is placed on the rear side of the backing load member 5. Then, since a plurality of division grooves 9 is formed by a mechanical process, the piezoelectric element 1 is divided into a plurality of components, and they are arrayed. This is a so-called array type. When the piezoelectric element 1 is divided by the mechanical process and the like, a notch is put up to the depth of a part of the backing load member 5. This is required in order that when the divided piezoelectric element 1 is vibrated individually and singly, the vibration is not transmitted through the backing load member 5 to the adjacent piezoelectric element 1, namely, acoustic crosstalk is reduced.

On the other hand, the block-shaped heat conduction member 6 placed on the rear surface of the backing load member 5 is configured to be continuously linked in the array direction of the piezoelectric elements 1. This is intended to easily absorb and radiate the heat as much as possible. In this way, when the heat conduction member 6 is configured as the block, if the heat conduction member 6 exists in the depth portion of the division groove 9 to the backing load member 5, the vibration is transmitted through the backing load member 5 and the heat conduction member 6 to the adjacent different piezoelectric element 1 as mentioned above, and acoustic crosstalk is increased. In particular, the material that is easy in acoustic transmission and small in attenuation is used for the heat conduction member 6. Thus, the configuration, where the heat conduction member 6 is placed at the depth that does not reach the division groove 9 of the piezoelectric element 1, can protect the acoustic crosstalk. The same materials as the materials explained in the first embodiment are used in the backing load member 5 and the heat conduction member 6 which are explained here.

With the above-mentioned configuration, the heat generated in the plurality of arrayed piezoelectric elements 1 and the heat generated by the multiple reflection can be transmitted through the heat conduction member 6 placed inside the backing load member 5 or the part thereof. Moreover, with the configuration for reducing the influence of the acoustic crosstalk caused by the heat conduction member 6, this has the effects that the deterioration in the resolution can be protected and that the surface temperature of the ultrasonic probe can be lowered. Hence, since the transmission voltage of the ultrasonic diagnostic apparatus can be made higher, the diagnostic depth can be made deeper.

Fifth Embodiment

Figure 7:
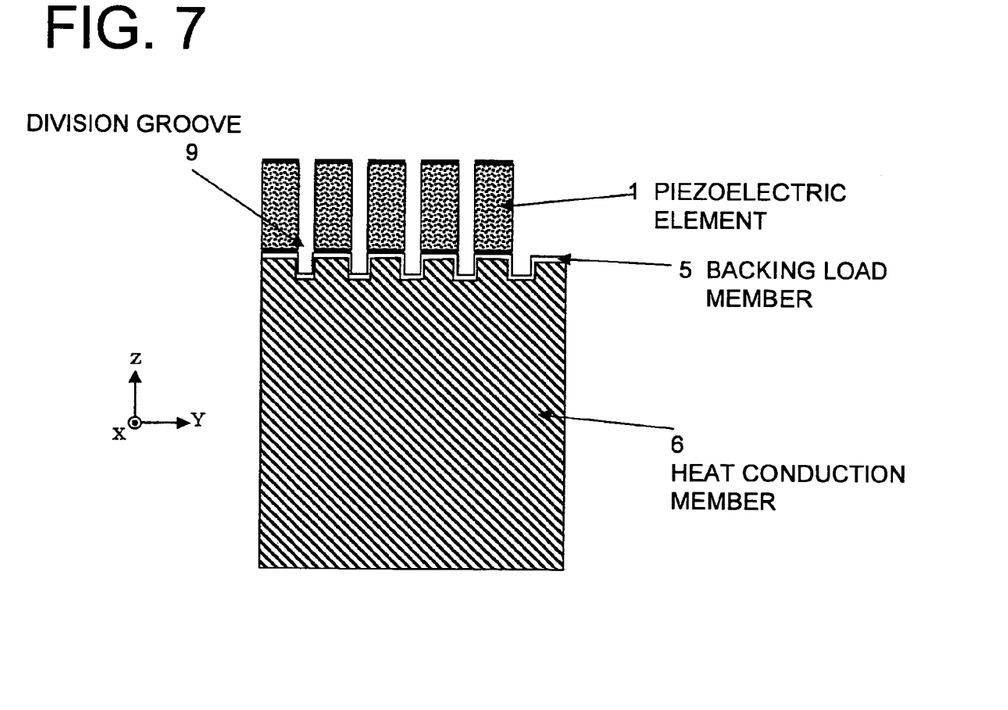
FIG. 7 is a schematic sectional view of an ultrasonic probe in a fifth embodiment of the present invention.

Also, as the fifth embodiment, as shown in FIG. 7, even in the configuration where the division grooves 9 are formed at the depth where they reach the block-shaped heat conduction member 6 and where a backing load member 5 is formed on the concave and convex surface formed on the surface of the heat conduction member 6 through the division grooves 9, the above-mentioned effect is obtained.

Sixth Embodiment

By the way, in the above-mentioned embodiments, the configuration where the piezoelectric elements 1 are one-dimensionally arrayed is explained. However, in addition to this, even in the configuration where the piezoelectric elements 1 are two-dimensionally arrayed, the similar effect is obtained.

INDUSTRIAL APPLICABILITY

The ultrasonic probe of the present invention can be used in another apparatus for obtaining an ultrasonic tomography image, in addition to the ultrasonic diagnostic apparatus.

The invention claimed is:

1. An ultrasonic probe comprising:
a piezoelectric element for transmitting and receiving ultrasonic waves, said piezoelectric element having a ground electrode and a first signal electrode on both surfaces thereof respectively;
a second signal electrode electrically connected to said first signal electrode;
a backing load member placed on a rear surface of said piezoelectric element; and
a heat conduction material which is placed inside said backing load member and which includes a thermal conductivity greater than a thermal conductivity of said backing load member, said heat conduction material being provided separately from said second signal electrode.

2. An ultrasonic probe comprising:
a plurality of piezoelectric elements, which are arrayed in one direction, for transmitting and receiving ultrasonic waves, each of said piezoelectric elements having a ground electrode and a first signal electrode on both surfaces respectively;
a plurality of second signal electrodes each of which is electrically connected to a respective one of said first signal electrodes;
a backing load member placed on rear surfaces of said plurality of piezoelectric elements; and
one or more sheet-shaped heat conduction materials which are placed in parallel along an array direction of said piezoelectric elements and a depth direction inside said backing load member and whose thermal conductivities are greater than a thermal conductivity of said backing load member, said heat conduction materials being provided separately from said second signal electrodes.

3. The ultrasonic probe according to claim 1, characterized in that an end portion of said piezoelectric element side of said heat conduction material has the shape inclined to a surface of said backing load member side of said piezoelectric element.

4. The ultrasonic probe according to claim 3, wherein an angle between an inclination plane of the end portion on said piezoelectric element side of said heat conduction material and a direction vertical to the rear side of said piezoelectric element is 40 degrees or less or an angle where a critical angle of the ultrasonic waves is subtracted from 90 degrees.

5. The ultrasonic probe according to claim 1, further comprising a heat radiating block which is connected to said heat conduction material and whose thermal conductivity is greater than the thermal conductivity of said backing load member.

6. The ultrasonic probe according to claim 5, wherein said heat radiating block is placed on the rear surface of said backing load member and wherein said heat conduction material is further placed between said heat radiating block and said backing load member.

7. The ultrasonic probe according to claim 1, wherein as said heat conduction material, any material of PUS graphite sheet with high degree of orientation where polymeric film is graphitized, graphite, carbon nano-tube, aluminum nitride, boron nitride, silicon carbide, beryllium oxide, copper and aluminum is used.

8. The ultrasonic probe according to claim 2 characterized in that an end portion of said piezoelectric element side of said heat conduction material has the shape inclined to a surface of said backing load member side of said piezoelectric element.

9. The ultrasonic probe according to claim 2, wherein as said heat conduction material, any material of PGS graphite sheet with high degree of orientation where polymeric film is graphitized, graphite, carbon nano-tube, aluminum nitride, boron nitride, silicon carbide, beryllium oxide, copper and aluminum is used.

* * * * *